United States Patent [19]

Izzo et al.

[11] 4,402,958
[45] Sep. 6, 1983

[54] NOVEL (SUBSTITUTED PHENYL)-1,2,4-TRIAZOLO (4,3-A)PYRAZINES AND NOVEL 2-HYDRAZINO-(SUBSTITUTED PHENYL)PYRAZINE INTERMEDIATES

[75] Inventors: Patrick T. Izzo, Pearl River, N.Y.; Robert A. Hardy, Jr., Ridgewood, N.J.

[73] Assignee: American Cyanamid Company, Stamford, Conn.

[21] Appl. No.: 323,109

[22] Filed: Nov. 19, 1981

[51] Int. Cl.³ .................. A61K 31/415; C07D 487/22
[52] U.S. Cl. ..................................... 424/250; 544/350
[58] Field of Search ......................... 544/350; 424/250

[56] References Cited
U.S. PATENT DOCUMENTS 3,594,479  7/1971  Maguire et al. ..................... 544/350
3,629,260 12/1971  Maguire et al. ..................... 544/350

OTHER PUBLICATIONS

G. Karmas and P. E. Spoerri, J. Amer. Chem. Soc., 74, 1580 (1952).
G. P. G. Dick, et al., J. Chem. Soc., 2131 (1956).
P. J. Lont and H. C. van der Plas, Rec. Trav. Chim., 92, 449 (1973).
H. Vanderhaege and M. Claesen, Bull. Soc. Chim. Beldg., 68, 30 (1959).
P. J. Helson and K. T Potts, J. Org. Chem., 27, 3243 (1962).
T. Huynh-Dinh, et al., J. Org. Chem., 44, 1028 (1979).
K. T. Potts and S. W. Schneller, J. Het. Chem., 5, 485 (1968).
Jones, "J. Amer. Chem. Soc.", 71, 78 (1949).

*Primary Examiner*—Donald G. Daus
*Assistant Examiner*—James H. Turnipseed
*Attorney, Agent, or Firm*—Mary-Ellen M. Timbers

[57] ABSTRACT

This disclosure describes novel 5-,6- and 8-(phenyl and substituted phenyl)-1,2,4-triazolo[4,3-a]pyrazines which posses utility as anxiolytic agents.

54 Claims, No Drawings

NOVEL (SUBSTITUTED PHENYL)-1,2,4-TRIAZOLO (4,3-A)PYRAZINES AND NOVEL 2-HYDRAZINO-(SUBSTITUTED PHENYL)PYRAZINE INTERMEDIATES

BRIEF SUMMARY OF THE INVENTION

This invention relates to new organic compounds and more particularly, is concerned with novel 5-,6- and 8-(phenyl or substituted phenyl)-1,2,4-triazolo[4,3-a]pyrazines which may be represented by the following structural formula:

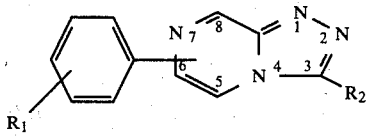
(X)

wherein $R_1$ is hydrogen, fluoro, chloro, trifluoromethyl, or alkoxy having from about one to three carbon atoms and $R_2$ is hydrogen or alkyl having from one to four carbon atoms. The invention is also concerned with novel 3-,5- and 6-(phenyl or substituted phenyl)-2-hydrazinopyrazine intermediates of the following general formula:

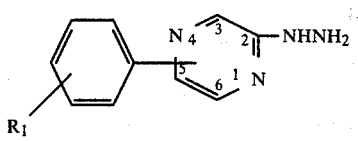
(VIII)

wherein $R_1$ is as hereinabove defined and the acid-addition salts thereof. The invention also includes compositions of matter containing the novel compounds (X) which are useful as anxiolytic agents and the method of meliorating anxiety in mammals therewith.

DETAILED DESCRIPTION OF THE INVENTION

The novel 5-,6- and 8-(phenyl or substituted phenyl)-1,2,4-triazolo[4,3-a]pyrazine compounds of the present invention are in general, off-white, tan or pink crystalline solids which are generally soluble in organic solvents such as chloroform, dichloromethane, tetrahydrofuran, acetone, N,N-dimethylformamide, acetic acid and lower alkanols.

Preparation of the novel 5-,6- or 8-(phenyl or substituted phenyl)-1,2,4-triazolo[4,3-a]pyrazine compounds of formula (X) of the instant invention which exhibit anxiolytic activity is carried out as outlined in Flowchart I. Preparation of the intermediates is outlined in Flowcharts II–IV.

FLOWCHART I
Preparation of (Phenyl and Substituted Phenyl)-1,2,4-Triazolo[4,3-a]pyrazines

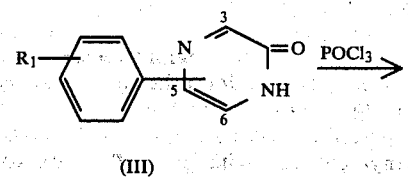

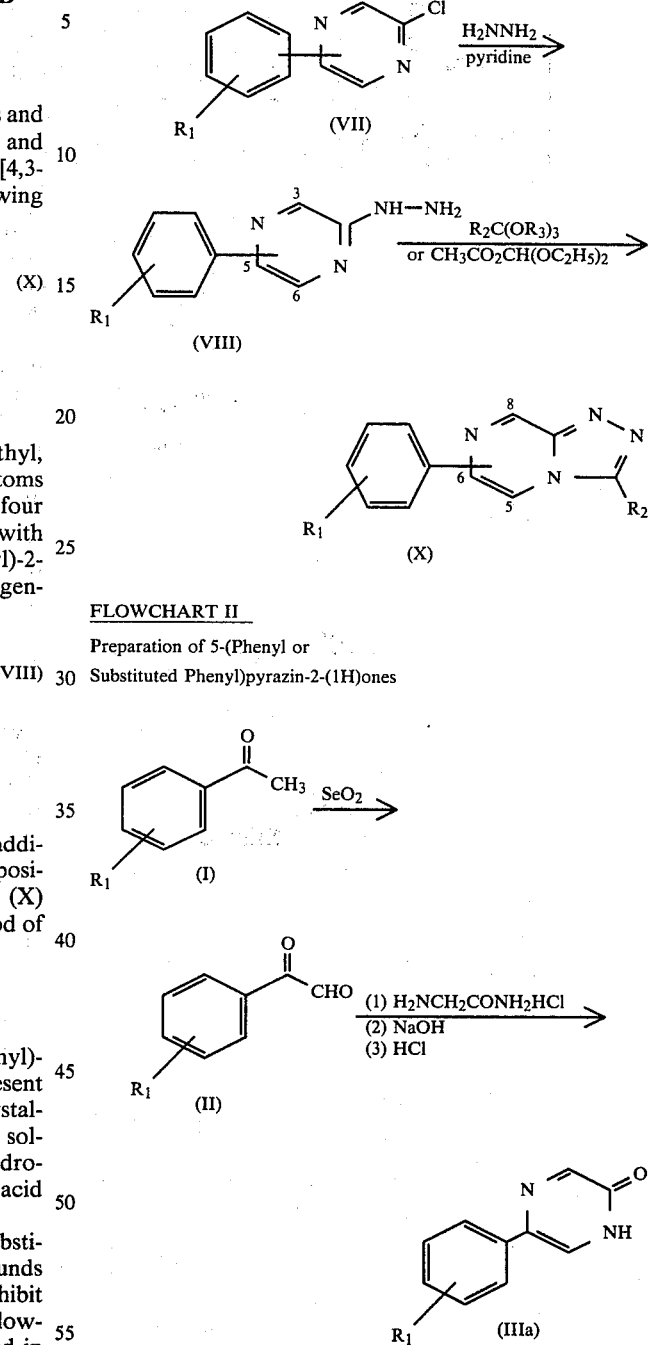

FLOWCHART III
Preparation of 3-(Phenyl or Substituted Phenyl)pyrazin-2(1H)ones

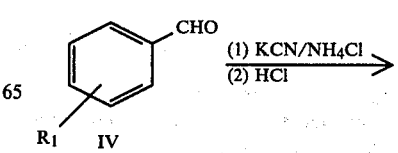

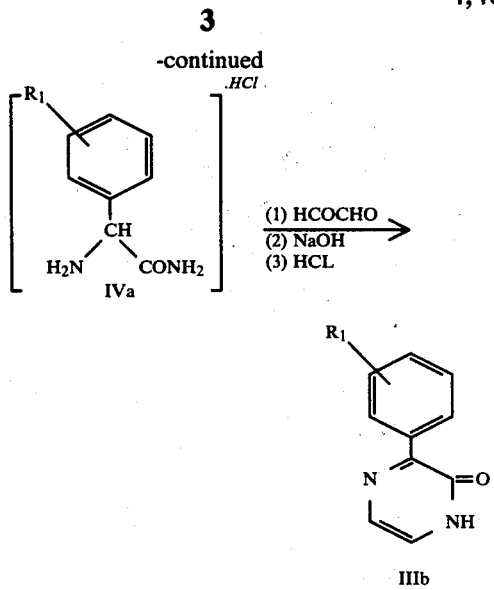

FLOWCHART IV
Preparation of 6-(Phenyl or substituted phenyl)pyrazin-2(1H)ones

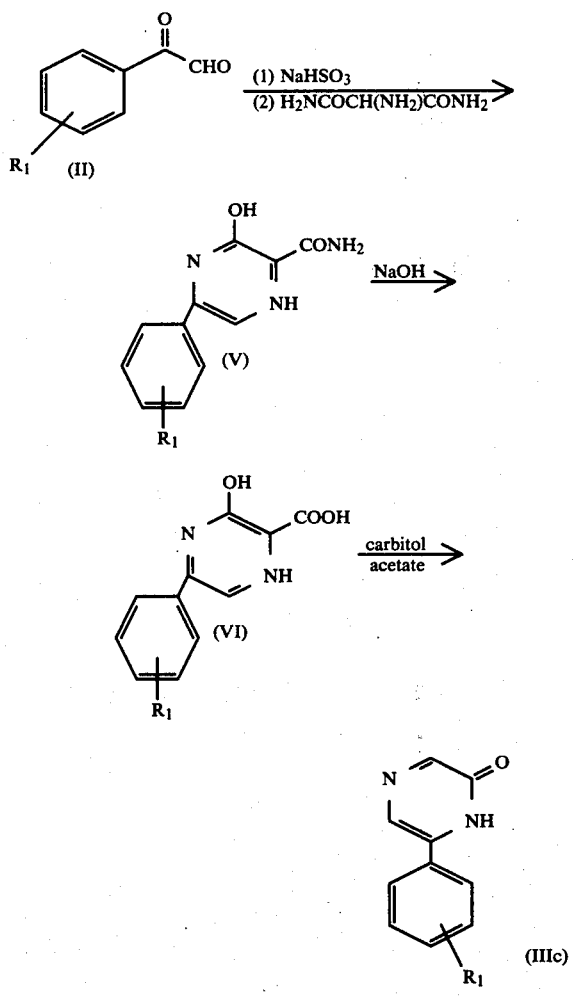

The corresponding 2-hydrazino-3-,5- and 6-(phenyl or substituted phenyl)pyrazine intermediate compound of formula (VIII), wherein $R_1$ is as above described, is reacted with a lower alkyl orthoformate, a lower alkyl orthoacetate, a lower alkyl orthopropionate or a lower alkyl orthobutyrate of the formula:

$$R_2-C(O-R_3)_3 \qquad (IX)$$

wherein $R_2$ is hydrogen or an alkyl substituent having from 1 through 4 carbon atoms such as methyl, ethyl, n-propyl or isopropyl and $R_3$ is methyl or ethyl.

An alternate reagent for the above cyclization is diethoxymethyl acetate [$CH_3COOCH(OC_2H_5)_2$]; in this case the cyclization product (X) has $R_2$ equal to hydrogen. Cyclization with diethoxymethyl acetate is usually complete in a short time; e.g. a few minutes at room temperature. At times it is also advantageous to carry out the initial part of the reaction in the cold to control the initial exothermic reaction and minimize by-product formation. The preferred temperature range is from about 0° C. to about 50° C.

In contrast, cyclization of the 3-,5- and 6-(phenyl or substituted phenyl)-2-hydrazinopyrazines (VIII), wherein $R_1$ is as above described, with orthoesters (IX), wherein $R_1$ and $R_2$ are as above described, requires more conventional time and temperature conditions, e.g., heating with an excess of the orthoester (IX) for about 1 to 5 hours. The hydrazine (VIII) is generally treated with an excess of the cyclizing reagent without additional solvent. The temperature range is from about 50° C. to about 150° C.; the refluxing temperature is commonly used.

The new products of this invention are readily identified by their spectral and physical properties. Both proton magnetic resonance spectra (1H-NMR) and ultraviolet spectra (UV) are characteristic.

The 2-hydrazino-3-,5- and 6-(phenyl or substituted phenyl)pyrazine intermediates (VIII), wherein $R_1$ is as above described, are readily prepared. For example, the 3-,5- and 6-(phenyl and substituted phenyl)-2-pyrazinones (III) wherein $R_1$ is as above described, are converted to the corresponding 2-chloro-3-,5- and 6-(substituted phenyl)-pyrazines (VII) wherein $R_1$ is as above described, by treatment with phosphorous oxychloride, followed by treatment of the chloro derivative with hydrazine in the presence of pyridine to give the desired hydrazino-pyrazine (VIII, Flowchart I).

The 3- or 5-(phenyl or substituted phenyl)-2-chloropyrazines may be prepared by methods described by G. Karmas and P. E. Spoerri, J. Am. Chem. Soc., 74, 1580, (1952) which is incorporated herein by reference. The 6-(phenyl or substituted phenyl)pyrazinones may be prepared by the procedures of Wood and Logan, J. Chem. Soc. 2131 (1956) and Lont and van der Plas, Rec. Trav. Chim., 92 455 (1953) which is incorporated herein by reference. Conversion of the chloropyrazines to the hydrazino-pyrazine intermediates (VIII) may also be effected by methods used for chloroheterocycles; e.g. hydrazinopyrimidines from chloropyrimidines; Vanderhaeghe and Claesen, Bull. Soc. Chim. Belg., 68, 30 (1959 [Chem. Abstr., 56, 10144i (1962)], which is incorporated herein by reference.

Preparation of the 5-(phenyl or substituted phenyl)-pyrazin-2(1H)ones of formula (IIIa), wherein $R_1$ is as described above, is outlined in Flowchart II. Substituted acetophenones of general Structure I, wherein $R_1$ is as above described, are oxidized with selenium dioxide ($SeO_2$) in water-dioxane to form the corresponding substituted phenyl-glyoxals of Structure (II), wherein $R_1$ is as above described. Treatment of the phenyl or substituted phenyl glyoxals with glycinamide hydrochloride in methanol-water at −40° C. followed sequentially by treatment with aqueous sodium hydroxide (NaOH) and acidification with concentrated hydrochloric acid (HCl) affords 5-(phenyl or substituted phenyl)pyrazin-2(1H)ones of general formula (IIIa), wherein $R_1$ is as above described.

The preparation of the 3-(phenyl or substituted phenyl)pyrazin-2(1H)ones of formula (IIIb), wherein $R_1$ is as described above, is outlined in Flowchart III. Sequential reaction of benzaldehyde or a substituted benzaldehyde of formula IV, wherein $R_1$ is as above described, with an aqueous solution of potassium cyanide (KCN) and ammonium chloride ($NH_4Cl$), followed by treatment with concentrated hydrochloric acid affords (phenyl or substituted phenyl)glycinamide hydrochloride (IVa), wherein $R_1$ is as above described. Treatment of glycinamide (IVa) with glyoxal (HCOCHO), and 10 N aqueous sodium hydroxide, followed by acidification with 10 N hydrochloric acid affords 3-(phenyl or substituted phenyl)pyrazin-2(1H)ones of general formula (IIIb), wherein $R_1$ is as above described.

The preparation of 6-(phenyl or substituted phenyl)-pyrazin-2(1H)ones of formula (IIIc), wherein $R_1$ is as above described, is outlined in Flowchart IV. Phenyl or substituted phenyl glyoxals of general formula (II), wherein $R_1$ is as above described, are prepared as described above. Reaction of II with aqueous sodium bisulfite ($NaHSO_3$), followed by addition of an aqueous solution of aminomalonamide ($H_2NCOCH(NH_2)CONH_2$) affords the 3-hydroxy-5-phenylpyrazine-2-carboxamide, V, wherein $R_1$ is as above described. The product is hydrolyzed with ethanolic sodium hydroxide to afford the 3-hydroxy-5-phenylpyrazine-2-carboxylic acid, VI, wherein $R_1$ is as above described. Treatment of VI with carbitol acetate at reflux temperature gives the 6-(phenyl or substituted phenyl)pyrazin-2(1H)ones of formula (IIIc), wherein $R_1$ is as described above.

The novel compounds of the present invention possess central nervous system activity at non-toxic doses and as such are useful as anxiolytic agents. That is, they produce certain responses in standard tests with laboratory animals which are known to correlate well with relief of anxiety in man. The compounds have been tested pharmacologically and found to have such properties with a desirable wide spread between doses producing anxiolytic activity and toxic symptoms.

The anti-anxiety properties of the novel compounds of the present invention are established in a test which indicates anxiolytic activity by the measure of protection from convulsions resulting from the administration of pentylenetetrazole. Single or graded dose levels of the test compounds are administered orally or intraperitoneally in a 2% starch vehicle, containing 0.5% v/v polyethylene glycol and one drop of polysorbate 80 to groups of at least 4 rats. At 30 or 60 minutes, the rats are treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York pp. 237–288 (1971)] that there is a high degree of correlation between antagonism of pentylenetetrazole seizures in rats and anti-anxiety effects in higher warm-blooded animals. The following representative compounds of the present invention listed in table I have been shown to possess anxiolytic activity when tested as described above.

TABLE I

Protection Against Clonic Seizures Caused By Pentylenetetrazole in Rats

| Compound | Results* |
| --- | --- |
| 6-Phenyl-1,2,4-triazolo[4,3-a]pyrazine | Active |
| 6-(3-Methoxyphenyl)-1,2,4-triazolo[4,3-a]pyrazine | Active |
| 8-(4-Chlorophenyl)-1,2,4-triazolo[4,3-a]pyrazine | Active |

*Test compounds are administered intraperitoneally at a dose of 50 mg./kg., 30 minutes before treatment with pentylenetetrazole.

The novel compounds of the present invention may be employed for meliorating anxiety in mammals when administered in amounts ranging from about 0.5 mg. to about 50.0 mg/kg. of body weight per day. A preferred dosage regimen for optimum results would be from about 1.0 mg. to about 10.0 mg./kg. of body weight per day. Such dosage units are employed that contain a total of from about 10 to about 200 mg. of active compound. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl, and propylparabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 25 to 50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 5 to 25 mg./ml. of active ingredient are satisfactory The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations would contain at least 0.1% of active compound. The percentage of the compositions and preparations may, of course, be varied and may conveniently be between about 2% and about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl, and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

5-Phenylpyrazin-2(1H)one

A solution of 2.2 g. (0.02 mol.) of glycinamide hydrochloride (Aldrich Chemical Co.) in 10 ml. of methanol and 4.0 ml. of water was cooled to −40° C. Similarly, 3.0 g. (0.02 mol.) of phenylglyoxal monohydrate (Aldrich Chemical Co.) was dissolved in 14 ml. methanol and cooled to −40° C. The two solutions were mixed and stirred while 3.6 ml. of a 12.5 N sodium hydroxide solution (0.045 mol.) is slowly added at such a rate as to maintain the temperature of the reaction mixture below −10° C. Stirring was continued for 2.0 hr. at −5° C., and then the reaction mixture was stored at 25° C. for 18 hrs. The reaction mixture was cooled to −5° C. and acidified with 2.0 ml. of concentrated hydrochloric acid. The resultant precipitate was isolated by filtration and washed with water, then recrystallized from ethanol to give 1.9 g. of the title compound.

EXAMPLE 2

5-Phenylpyrazin-2(1H)one

A suspension of 11.1 g. (0.1 mol.) of selenium dioxide in 75 ml. of dioxane and 2.2 ml. of water is stirred for 0.5-2.0 hrs. at 60°-70° C. until the selenium dioxide was completely dissolved. Acetophenone (0.1 mol.) is added in one portion and the reaction mixture is refluxed for 5.0 hr. The resultant suspension is filtered through Celite ® until clear and the filtrate treated with 100 g. of ice and a 0° C. solution of 0.1 mol. of glycinamide hydrochloride in 70 ml. of methanol and 20 ml. of water. The mixture is stirred while adding 18 ml. of a 12.5 N sodium hydroxide solution while maintaining the temperature of the reaction mixture at about −10° C. The reaction mixture is stirred for 1 hr. at 0° C. then warmed to 25° C. over 2.0 hr. The reaction mixture is acidified with 12.0 ml. of concentrated hydrochloric acid while applying external ice cooling. The title product precipitates as a rust colored solid which is isolated and purified as described in Example 1.

EXAMPLE 3

3-Phenylpyrazin-2(1H)one

To a stirred solution of 0.3 mol. of potassium cyanide and 0.3 mol. of ammonium chloride in 100 ml. of water is added a solution of 0.3 mol. of benzaldehyde (Aldrich Chemical Co.) in 100 ml. of methanol. The reaction mixture is stirred at 25° C. for 6.0 hr. The oil layer is isolated and dissolved in methylene chloride. The solution is washed with water, dried and evaporated to give a brown oil. The oil is stirred with 150 ml. of concentrated hydrochloric acid for 1.0 hr. at 45° C. to precipitate phenylglycinamide hydrochloride. The precipitate is dissolved in 120 ml. of water stirred and cooled to 2° C. A solution of 4.8 g. (0.03 mol.) of 40% aqueous glyoxal is added, followed by dropwise addition of 6.0 ml. of 10 N sodium hydroxide. The reaction mixture is stirred for 5.0 hr. at 2° C. and then filtered. The filtrate is acidified to pH 6 with 3.0 ml. of 10 N hydrochloric acid and the precipitate of title compound is collected by filtration.

EXAMPLES 4-9

The following 3-(substituted phenyl)pyrazin-2(1H) ones listed in Table II are prepared from the corresponding substituted benzaldehydes (Aldrich Chemical Co.) according to the procedure of Example 3.

TABLE II

| Example | Substituted Benzaldehyde | 3-(Substituted phenyl) pyrazin-2(1H)one |
|---|---|---|
| 4 | 4-chlorobenzaldehyde | 3-(4-chlorophenyl)pyrazin-2(1H)one |
| 5 | 4-methoxybenzaldehyde | 3-(4-methoxyphenyl) pyrazin-2(1H)one |
| 6 | 4-fluorobenzaldehyde | 3-(4-fluorophenyl) pyrazin-2(1H)one |
| 7 | 3-chlorobenzaldehyde | 3-(3-chlorophenyl) pyrazin-2-(1H)one |
| 8 | 3-ethoxybenzaldehyde | 3-(3-ethoxyphenyl) pyrazin-2(1H)one |
| 9 | 3-trifluoromethylbenzaldehyde | 3-(3-trifluoromethylphenyl)pyrazin-2(1H)one |

EXAMPLES 10-16

The following 5-(substituted phenyl)pyrazin-2(1H)ones listed in Table III are prepared from the corresponding substituted acetophenones according to the procedure of Example 2.

TABLE III

| Example | Substituted acetophenone | 5-(substituted phenyl) pyrazin-2(1H)one |
|---|---|---|
| 10 | 3-chloroacetophenone | 5-(3-chlorophenyl) pyrazin-2(1H)one |
| 11 | 3-methoxyacetophenone | 5-(3-methoxyphenyl) pyrazin-2(1H)one |
| 12 | 4-chloroacetophenone | 5-(4-chlorophenyl) pyrazin-2(1H)one |
| 13 | 4-trifluoromethyl-acetophenone | 5-(4-trifluoromethyl-phenyl)pyrazin-2(1H)one |
| 14 | 2-fluoroacetophenone | 5-(2-fluorophenyl) pyrazin-2(1H)one |
| 15 | 4-isopropoxyaceto-phenone | 5-(4-isopropoxyphenyl) pyrazin-2(1H)one |
| 16 | 2-chloroacetophenone | 5-(2-chlorophenyl) pyrazin-2(1H)one |

EXAMPLE 17

6-Phenylpyrazin-2(1H)one

A solution of 5.4 g. of phenylglyoxal hydrate in 25 ml. water is treated with 50 ml. of aqueous sodium bisulfite (density 1.34) at 25° C. for 45 min. A solution of 3.9 g. of aminomalonamide in 39 ml. of water is added and the reaction mixture is heated at 100° C. for 2.5 hr. The resultant yellow precipitate which forms is isolated by filtration, washed with water, dried and recrystallized from ethanol to afford 3-hydroxy-5-phenylpyrazine-2-carboxamide. This product is hydrolyzed with saturated ethanolic sodium hydroxide for 16 hrs. at 150° C. to afford 3-hydroxy-5-phenylpyrazine-2-carboxylic acid. This product is refluxed with 30 ml. of carbitolacetate for 15 min. then cooled to 250° C. and petroleum ether (bp 68° C.) added to precipitate the title compound.

EXAMPLES 18–22

The following 6-(substituted phenyl)pyrazin-2(1H)ones listed in Table IV are prepared from the corresponding substituted phenylglyoxals according to the procedure of Example 17.

TABLE IV

| Example | Substituted Phenylglyoxal | 6-(Substituted phenyl)-pyrazin-2(1H)one |
|---|---|---|
| 18 | 3-methoxyphenylglyoxal | 6-(3-methoxyphenyl)-pyrazin-2(1H)one |
| 19 | 4-ethoxyphenylglyoxal | 6-(4-ethoxyphenyl)-pyrazin-2(1H)one |
| 20 | 3-trifluoromethylphenyl-glyoxal | 6-(3-trifluoromethyl-phenyl)-pyrazin-2(1H)one |
| 21 | 2-chlorophenylglyoxal | 6-(2-chlorophenyl)-pyrazin-2(1H)one |
| 22 | 4-fluorophenylglyoxal | 6-(4-fluorophenyl)-pyrazin-2(1H)one |

EXAMPLE 23

2-Chloro-3-phenylpyrazine

A 0.01 mol. sample of 3-phenylpyrazin-2(1H)one is mixed with 9.0 ml. of phosphorous oxychloride (POCl$_3$) and refluxed for 5–6 hr. The excess phosphorous oxychloride is removed by distillation at reduced pressure and 25 ml. of methylene chloride added to the residue. The resultant solution is stirred with a few milliliters of ice water, dried, evaporated and the residue recrystallized to yield the title compound.

EXAMPLES 24–29

The following 2-chloro-3-(substituted phenyl)pyrazines listed in Table IV are prepared from the corresponding 3-(substituted phenyl)pyrazin-2(1H)ones according to the procedure of Example 23.

TABLE V

| Example | 3-(Substituted-phenyl) pyrazin-2(1H)one | 2-Chloro-3-(substituted phenyl)pyrazine |
|---|---|---|
| 24 | 3-(4-chlorophenyl)-pyrazin-2(1H)one | 2-chloro-3-(4-chloro-phenyl)-pyrazine |
| 25 | 3-(4-methoxyphenyl)-pyrazin-2(1H)one | 2-chloro-3-(4-methoxy-phenyl)-pyrazine |
| 26 | 3-(4-fluorophenyl)-pyrazin-2(1H)one | 2-chloro-3-(4-fluoro-phenyl)pyrazine |
| 27 | 3-(3-chlorophenyl)-pyrazin-2(1H)one | 2-chloro-3-(3-chloro-phenyl)pyrazine |
| 28 | 3-(3-ethoxyphenyl)-pyrazin-2(1H)one | 2-chloro-3-(3-ethoxy-phenyl)pyrazine |
| 29 | 3-(3-trifluoromethyl-phenyl)pyrazin-2(1H)one | 2-chloro-3-(3-trifluoro-methylphenyl)pyrazine |

EXAMPLE 30

2-Chloro-5-phenyl-pyrazine

A mixture of 0.01 mol. of 5-phenylpyrazin-2(1H)one 8.0 ml. of POCl$_3$ and a drop of concentrated sulfuric acid is refluxed for 4–5 hr. The solution is poured into 100 g. of ice. The title compound is isolated by filtration and recrystallized.

EXAMPLES 31–41

The following 2-chloro-5- and 6-(phenyl and substituted phenyl)pyrazines listed in Table VI are prepared from the corresponding 5- and 6-(phenyl and substituted phenyl)pyrazin-2(1H)ones according to the procedure of Example 30.

TABLE VI

| Example | 5- and 6-(substituted phenyl)pyrazin-2(1H)one | 2-Chloro-5- and 6-(phenyl or substituted phenyl)pyrazine |
|---|---|---|
| 31 | 5-(3-chlorophenyl)-pyrazin-2(1H)one | 2-chloro-5-(3-chloro-phenyl)pyrazine |
| 32 | 5-(3-methoxyphenyl)-pyrazin-2(1H)one | 2-chloro-5-(3-methoxy-phenyl)pyrazine |
| 33 | 5-(4-chlorophenyl)-pyrazin-2(1H)one | 2-chloro-5-(4-chloro-phenyl)pyrazine |
| 34 | 5-(4-trifluoromethyl-phenyl)pyrazin-2(1H)one | 2-chloro-5-(4-trifluoro-methylphenyl)pyrazine |
| 35 | 5-(2-fluorophenyl)-pyrazin-2(1H)one | 2-chloro-5-(2-fluorophenyl)-pyrazine |
| 36 | 5-(4-isopropoxy-phenyl)pyrazin-2(1H)one | 2-chloro-5-(4-isopropoxy-phenyl)pyrazine |
| 37 | 5-(2-chlorophenyl)-pyrazin-2(1H)one | 2-chloro-5-(2-chloro-phenyl)pyrazine |
| 38 | 6-(3-methoxyphenyl)-pyrazin-2(1H)one | 2-chloro-6-(3-methoxy-phenyl)pyrazine |
| 39 | 6-(4-ethoxyphenyl)-pyrazine-2(1H)one | 2-chloro-6-(4-ethoxy-phenyl)pyrazine |
| 40 | 6-(3-trifluoromethyl-phenyl)pyrazin-2(1H)one | 2-chloro-6-(3-trifluoro-methylphenyl)pyrazine |
| 41 | 6-(2-chlorophenyl)-pyrazin-2(1H)one | 2-chloro-6-(2-chloro-phenyl)pyrazine |
| 42 | 6-(4-fluorophenyl)-pyrazin-2(1H)one | 2-chloro-6-(4-fluoro-phenyl)pyrazine |
| 43 | 6-phenyl-pyrazin-2(1H)one | 2-chloro-6-phenylpyrazine |

EXAMPLE 44

2-Hydrazino-5-phenylpyrazine

A mixture of 1.0 g. of 2-chloro-5-phenylpyrazine, m.p. 98°–99° C., 5.0 ml. of pyridine and 5.0 ml. of hydrazine hydrate is heated at reflux for 1.5 hours. The solution is cooled, and 20 ml. of water is added. The colorless crystalline product is collected and air dried. The crude product is recrystallized from aqueous ethanol to yield 0.35 g. of the product of the example as colorless needles, m.p. 128°–130° C.

EXAMPLES 45–64

The following 2-hydrazino-3-,5- and 6-(phenyl and substituted phenyl)pyrazines listed in Table VII are prepared from the corresponding 2-chloro-3-,5-, and 6-(phenyl and substituted phenyl)pyrazines according to the procedure of Example 44.

TABLE VII

| Example | 2-Chloro-3-, 5- and 6-phenyl pyrazine (Starting material) | m.p. °C. | 2-Hydrazino-3-, 5- and 6-phenyl pyrazine (Product) | m.p. °C. | Description |
|---|---|---|---|---|---|
| 45 | 2-Chloro-5-(3-chlorophenyl)-pyrazine | 117–119 | 2-Hydrazino-5-(3-chlorophenyl)-pyrazine | 125–127 | Yellow Needles |
| 46 | 2-Chloro-5-(3-methoxyphenyl)-pyrazine | 91–93 | 2-Hydrazino-5-(3-methoxyphenyl)-pyrazine | 103–105 | Tan Crystals |
| 47 | 2-Chloro-5-(4-chlorophenyl)-pyrazine | 142–143 | 2-Hydrazino-5-(4-chlorophenyl)-pyrazine | 139–142 | Tan Crystals |
| 48 | 2-Chloro-5-(4-trifluoromethyl-phenyl)pyrazine | — | 2-Hydrazino-5-(4-trifluoromethyl-phenyl)pyrazine | — | — |
| 49 | 2-Chloro-5-(2-fluorophenyl)-pyrazine | — | 2-Hydrazino-5-(2-fluorophenyl)-pyrazine | — | — |
| 50 | 2-Chloro-5-(4-isopropoxyphenyl)-pyrazine | — | 2-Hydrazino-5-(4-isopropoxyphenyl)-pyrazine | — | — |
| 51 | 2-Chloro-5-(2-chlorophenyl)-pyrazine | — | 2-Hydrazino-5-(2-chlorophenyl)-pyrazine | — | — |
| 52 | 2-Chloro-3-phenyl-pyrazine | 65–68 | 2-Hydrazino-3-phenylpyrazine dihydrochloride | 182–184 (Dec.) | Yellow Crystals |
| 53 | 2-Chloro-3-(4-methoxyphenyl)-pyrazine | 104–106 | 2-Hydrazino-3-(4-methoxyphenyl)-pyrazine | Not Recrystallized | Oil |
| 54 | 2-Chloro-3-(4-chlorophenyl)-pyrazine | 132–135 | 2-Hydrazino-3-(4-chlorophenyl)-pyrazine | 115–117 | Brown Crystals |
| 55 | 2-Chloro-3-(4-fluorophenyl)-pyrazine | — | 2-Hydrazino-3-(4-fluorophenyl)-pyrazine | — | — |
| 56 | 2-Chloro-3-(3-chlorophenyl)pyrazine | — | 2-Hydrazino-3-(3-chlorophenyl)-pyrazine | — | — |
| 57 | 2-Chloro-3-(3-ethoxyphenyl)-pyrazine | — | 2-Hydrazino-3-(2-ethoxyphenyl)-pyrazine | — | — |
| 58 | 2-Chloro-3-(3-trifluoromethyl-phenyl)pyrazine | — | 2-Hydrazino-3-(3-trifluoromethyl-phenyl)pyrazine | — | — |
| 59 | 2-Chloro-6-(3-methoxyphenyl)-pyrazine | — | 2-Hydrazino-6-(3-methoxyphenyl)-pyrazine | — | — |
| 60 | 2-Chloro-6-(4-ethoxyphenyl)-pyrazine | — | 2-Hydrazino-6-(4-ethoxyphenyl)-pyrazine | — | — |
| 61 | 2-Chloro-6-(3-trifluoromethyl-phenyl)pyrazine | — | 2-Hydrazino-6-(3-trifluoromethyl-phenyl)pyrazine | — | — |
| 62 | 2-Chloro-6-(2-chlorophenyl)-pyrazine | — | 2-Hydrazino-6-(2-chlorophenyl)-pyrazine | — | — |
| 63 | 2-Chloro-6-phenylpyrazine | — | 2-Hydrazino-6-phenylpyrazine | — | — |
| 64 | 2-Chloro-6-(4-fluorophenyl)-pyrazine | — | 2-Hydrazino-6-(4-fluorophenyl)-pyrazine | — | — |

EXAMPLE 65

6-Phenyl-1,2,4-triazolo[4,3-a]pyrazine

To 5 ml. of stirred diethoxymethyl acetate at room temperature is added, in portions, 0.67 g. (0.0036 mole), of 2-hydrazino-5-phenylpyrazine. A slight heat evolution is observed and the hydrazino compound rapidly dissolves. After a short time the product precipitates. Stirring is continued for another 1–2 hours and the product is collected and recrystallized from ethanol to give 0.53 g. of 6-phenyl-1,2,4-triazolo[4,3-a]pyrazine, m.p. 231°–233° C.

EXAMPLE 66

6-Phenyl-3-methyl-1,2,4-triazolo[4,3-a]pyrazine

A solution of 0.5 g. (0.0027 mole) of 2-hydrazino-5-phenylpyrazine in 5.0 ml. of triethyl orthoacetate is heated under reflux for 5 hours. The crystalline product precipitates from the hot reaction solution, and at the end of the heating period the mixture is cooled and the product is collected. Recrystallization from ethanol gives 0.36 g. of the product of the example, m.p. 192°–195° C.

EXAMPLES 67 TO 71

Procedures similar to those described in Examples 65 and 66 are employed to prepare the additional substituted 6-phenyl-1,2,4-triazolo[4,3-a]pyrazine compounds listed in Table VIII.

room temperature and after one hour the precipitated product is collected, washed with ethanol and air dried. The crude product is recrystallized from acetonitrile to yield 1.1 g. of the product of the example as tan needles, m.p. 238°–239° C.

EXAMPLE 73

8-Phenyl-3-methyl-1,2,4-triazolo[4,3-a]pyrazine

A solution of 0.78 g. of 2-hydrazino-3-phenylpyrazine in 6.0 ml. of triethyl orthoacetate is heated under reflux for one hour. The reaction mixture is cooled in an ice bath and the precipitated solid is collected by filtration. The solid is recrystallized from ethanol to give 0.49 g. of the desired product as tan crystals, m.p. 178°–180° C.

EXAMPLES 74 TO 77

Procedures similar to those described in Examples 72 and 73 are employed to prepare the additional 8-phenyl-1,2,4-triazolo[4,3-a]pyrazine compounds listed in Table IX.

TABLE VIII

| Example | Starting Material 2-Hydrazino-5-phenyl pyrazine | Procedure Used | Product | m.p. °C. | Crystallization Solvent |
|---|---|---|---|---|---|
| 67 | 2-Hydrazino-5-(3-chlorophenyl)-pyrazine | Ex. 65 | 6-(3-Chlorophenyl)-1,2,4-triazolo-[4,3-a]pyrazine | 271–273 | Acetonitrile |
| 68 | 2-Hydrazino-5-(3-chlorophenyl)-pyrazine | Ex. 66 | 6-(3-Chlorophenyl)-3-methyl-1,2,4-triazolo[4,3-a]-pyrazine | 225–227 | Ethanol |
| 69 | 2-Hydrazino-5-(3-methoxyphenyl)-pyrazine | Ex. 65 | 6-(3-Methoxyphenyl)-1,2,4-triazolo[4,3-a]pyrazine | 171–173 | Ethanol |
| 70 | 2-Hydrazino-5-(3-methoxyphenyl)-pyrazine | Ex. 66 | 6-(3-Methoxyphenyl)-3-methyl-1,2,4-triazolo[4,3-a]-pyrazine | 167–169 | Ethanol |
| 71 | 2-Hydrazino-5-(4-chlorophenyl)-pyrazine | Ex. 65 | 6-(4-Chlorophenyl)-1,2,4-triazolo-[4,3-a]pyrazine | 272–274 | Acetonitrile |

TABLE IX

| Example | Starting Material 2-Hydrazino-3-phenyl pyrazine | Procedure Used | Product | m.p. °C. | Crystallization Solvent |
|---|---|---|---|---|---|
| 74 | 2-Hydrazino-3-(4-methoxyphenyl)-pyrazine | Ex. 72 | 8-(4-Methoxyphenyl)-1,2,4-triazolo-[4,3-a]pyrazine | 206–207 | Ethanol |
| 75 | 2-Hydrazino-3-(4-methoxyphenyl)-pyrazine | Ex. 73 | 8-(4-Methoxyphenyl)-3-methyl-1,2,4-triazolo[4,3-a]-pyrazine | 173–175 | Ethanol |
| 76 | 2-Hydrazino-3-(4-chlorophenyl)-pyrazine | Ex. 72 | 8-(4-Chlorophenyl)-1,2,4-triazolo-[4,3-a]pyrazine | 238–240 | Ethanol |
| 77 | 2-Hydrazino-3-(4-chlorophenyl)-pyrazine | Ex. 73 | 8-(4-Chlorophenyl)-3-methyl-1,2,4-triazolo[4,3-a]-pyrazine | 247–249 | Ethanol |

EXAMPLE 72

8-Phenyl-1,2,4-triazolo[4,3-a]pyrazine

To 10 ml. of stirred diethoxymethyl acetate at room temperature is added, in portions, 2.0 g. of 2-hydrazino-3-phenylpyrazine. The reaction mixture is stirred at

EXAMPLES 78 TO 95

Procedures similar to those described in Examples 65 and 66 are utilized to prepare both the starting materials and final products listed in Table X.

TABLE X

| Example | Hydrazine (Starting Material) | Procedure | Product |
|---|---|---|---|
| 78 | 2-Hydrazino-6-phenylpyrazine | Ex. 65 | 5-Phenyl-1,2,4-triazolo-[4,3-a]pyrazine |

TABLE X-continued

| Example | Hydrazine (Starting Material) | Procedure | Product |
|---|---|---|---|
| 79 | 2-Hydrazino-5-(3-trifluoro-methylphenyl)pyrazine | Ex. 65 | 6-(3-Trifluoromethylphenyl)-1,2,4-triazolo[4,3-a]pyrazine |
| 80 | 2-Hydrazino-3-(2-chloro-phenyl)pyrazine | Ex. 65 | 8-(2-Chlorophenyl)-1,2,4-triazolo[4,3-a]pyrazine |
| 81 | 2-Hydrazino-5-(4-chloro-phenyl)pyrazine (with tri-ethyl orthopropionate) | Ex. 66 | 6-(4-Chlorophenyl)-3-ethyl-1,2,4-triazolo[4,3-a]pyrazine |
| 82 | 2-Hydrazino-6-(3-methoxy-phenyl)pyrazine | Ex. 65 | 5-(3-Methoxyphenyl)1,2,4-triazolo[4,3-1]pyrazine |
| 83 | 2-Hydrazino-5-(4-fluoro-phenyl)pyrazine | Ex. 66 | 6-(4-Fluorophenyl)-3-methyl-1,2,4-triazolo[4,3-a]pyrazine |
| 84 | 2-Hydrazino-6-(4-ethoxy-phenyl)pyrazine | Ex. 66 | 5-(4-ethoxyphenyl)-3-methyl-1,2,4-triazolo-8 4,3-a]-pyrazine |
| 85 | 2-Hydrazino-6-(3-trifluoro-methylphenyl)pyrazine (with triethylorthoisobutyrate) | Ex. 66 | 5-(3-trifluoromethylphenyl)-3-isopropyl-1,2,4-triazolo-[4,3-a]pyrazine |
| 86 | 2-Hydrazino-6-(2-chloro-phenyl)pyrazine (with triethylorthopropionate) | Ex. 66 | 5-(2-chlorophenyl)-3-ethyl-1,2,4-triazolo[4,3-a]-pyrazine |
| 87 | 2-Hydrazino-6-(4-fluoro-phenyl)pyrazine | Ex. 66 | 5-(4-fluorophenyl)-3-methyl-1,2,4-triazolo[4,3-a]pyrazine |
| 88 | 2-Hydrazino-5-(4-trifluoro-methylphenyl)pyrazine | Ex. 66 | 6-(4-trifluoromethylphenyl)-3-methyl-1,2,4-triazolo[4,3-a]pyrazine |
| 89 | 2-Hydrozino-s-(2-fluoro-phenyl)pyrazine (with triethylorthopropionate) | Ex. 66 | 6-(2-fluorophenyl)-3-ethyl-1,2,4-triazolo[4,3-a]-pyrazine |
| 90 | 2-Hydrazino-5-(4-isopro-poxyphenyl)pyrazine | Ex. 65 | 6-(4-isopropoxyphenyl)-1,2,4-triazolo[4,3-a]pyrazine |
| 91 | 2-Hydrazino-5-(2-chloro-phenyl)pyrazine (with triethylorthobutyrate) | Ex. 66 | 6-(2-chlorophenyl)-3-n-propyl-1,2,4-triazolo[4,3-a]pyrazine |
| 92 | 2-Hydrazino-3-(4-fluoro-phenyl)pyrazine (with triethylorthopropionate) | Ex. 66 | 8-(4-fluorophenyl)-3-ethyl-1,2,4-triazolo[4,3-a]pyrazine |
| 93 | 2-Hydrazino-3-(3-chloro-phenyl)pyrazine (with triethylorthoisobutyrate) | Ex. 66 | 8-(3-chlorophenyl)-3-isopropyl-1,2,4-triazolo[4,3-a]pyrazine |
| 94 | 2-Hydrazino-3-(2-ethoxy-phenyl)pyrazine (with triethylorthopropionate) | Ex. 66 | 8-(2-ethoxyphenyl)-3-ethyl-1,2,4-triazolo[4,3-a]pyrazine |
| 95 | 2-Hydrazino-3-(3-trifluoro-methylphenyl)pyrazine | Ex. 66 | 8-(3-trifluoromethylphenyl)-3-methyl-1,2,4-triazolo[4,3-a]pyrazine |

We claim:

1. A compound of the formula:

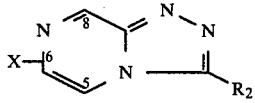

wherein X is

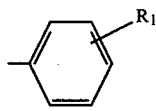

located on the 5, 6 or 8 carbon of said compound and $R_1$ is selected from the group consisting of hydrogen, fluoro, chloro, trifluoromethyl and $C_1$-$C_3$ alkoxy and wherein $R_2$ is hydrogen or $C_1$-$C_4$ alkyl.

2. The compound according to claim 1 of the formula:

3. The compound according to claim 1

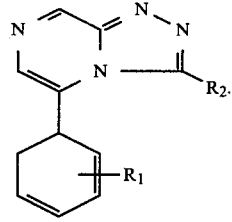

4. The compound according to claim 1

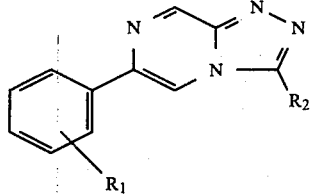

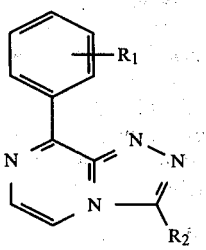

5. The compound according to claim 2 or claim 3 or claim 4 wherein $R_1$ is selected from the group consisting of para-ethoxy, meta-trifluoromethyl, ortho-chloro, para-chloro, para-fluoro, ortho-fluoro, meta-methoxy, para-trifluoromethyl, para-isopropoxy, meta-chloro, para-methoxy, ortho-ethoxy and hydrogen.

6. The compound according to claim 5 wherein $R_1$ is selected from the group consisting of hydrogen, meta-methoxy and para-chloro.

7. The compound according to claim 2 or claim 3 or claim 4 wherein $R_2$ is selected from the group consisting of methyl, ethyl, isopropyl and hydrogen.

8. The compound according to claim 2 wherein $R_1$ is para-ethoxy and $R_2$ is methyl; 5-(4-ethoxyphenyl)-3-methyl-1,2,4-triazolo[4,3-a]pyrazine.

9. The compound according to claim 2 wherein $R_1$ is meta-trifluoromethyl and $R_2$ is isopropyl; 5-(3-trifluoromethylphenyl-3-isopropyl-1,2,4-triazolo[4,3-a]pyrazine.

10. The compound according to claim 2 wherein $R_1$ is ortho-chloro and $R_2$ is ethyl; 5-(2-chlorophenyl)-3-ethyl-1,2,4-triazolo[4,3-a]pyrazine.

11. The compound according to claim 2 wherein $R_1$ is para-fluoro and $R_2$ is methyl; 5-(4-fluorophenyl)-3-methyl-1,2,4-triazolo[4,3-a]pyrazine.

12. The compound according to claim 2 wherein $R_1$ and $R_2$ are hydrogen; 5-phenyl-1,2,4-triazolo[4,3-a]pyrazine.

13. The compound according to claim 2 wherein $R_1$ is meta-methoxy and $R_2$ is hydrogen; 5-(3-methoxyphenyl)-1,2,4-triazolo[4,3-a]pyrazine.

14. The compound according to claim 3 wherein $R_1$ is para-trifluoromethyl and $R_2$ is methyl; 6-(4-trifluoromethylphenyl)-3-methyl-1,2,4-triazolo[4,3-a]pyrazine.

15. The compound according to claim 3 wherein $R_1$ is ortho-fluoro and $R_2$ is ethyl; 6-(2-fluorophenyl)-3-ethyl-1,2,4-triazolo[4,3-a]pyrazine.

16. The compound according to claim 3 wherein $R_1$ is para-isopropoxy and $R_2$ is hydrogen; 6-(4-isopropoxyphenyl)-1,2,4-triazolo[4,3-a]pyrazine.

17. The compound according to claim 3 wherein $R_1$ is ortho-chloro and $R_2$ is n-propyl; 6-(2-chlorophenyl)-3-n-propyl-1,2,4-triazolo[4,3-a]pyrazine.

18. The compound according to claim 3 wherein $R_1$ is meta-methoxy and $R_2$ is hydrogen; 6-(3-methoxyphenyl)-1,2,4-triazolo[4,3-a]pyrazine.

19. The compound according to claim 3 wherein $R_1$ is meta-chloro and $R_2$ is hydrogen; 6-(3-chlorophenyl)-1,2,4-triazolo[4,3-a]pyrazine.

20. The compound according to claim 3 wherein $R_1$ is meta-methoxy and $R_2$ is methyl; 6-(3-methoxyphenyl)-3-methyl-1,2,4-triazolo[4,3-a]pyrazine.

21. The compound according to claim 3 wherein $R_1$ is meta-chloro and $R_2$ is methyl; 6-(3-chlorophenyl)-3-methyl-1,2,4-triazolo[4,3-a]pyrazine.

22. The compound according to claim 3 wherein $R_1$ is para-chloro and $R_2$ is hydrogen; 6-(4-chlorophenyl)-1,2,4-triazolo[4,3-a]pyrazine.

23. The compound according to claim 3 wherein $R_1$ is hydrogen and $R_2$ is hydrogen; 6-phenyl-1,2,4-triazolo[4,3-a]pyrazine.

24. The compound according to claim 3 wherein $R_1$ is hydrogen and $R_2$ is methyl; 6-phenyl-3-methyl-1,2,4-triazolo[4,3-a]pyrazine.

25. The compound according to claim 4 wherein $R_1$ is para-fluoro and $R_2$ is ethyl; 8-(4-fluorophenyl)-3-ethyl-1,2,4-triazolo[4,3-a]pyrazine.

26. The compound according to claim 4 wherein $R_1$ is meta-chloro and $R_2$ is isopropyl; 8-(3-chlorophenyl)-3-isopropyl-1,2,4-triazolo[4,3-a]pyrazine.

27. The compound according to claim 4 wherein $R_1$ is ortho-ethoxy and $R_2$ is ethyl; 8-(2-ethoxyphenyl)-3-ethyl-1,2,4-triazolo[4,3-a]pyrazine.

28. The compound according to claim 4 wherein $R_1$ is meta-trifluoromethyl and $R_2$ is methyl; 8-(3-trifluoromethylphenyl)-3-methyl-1,2,4-triazolo[4,3,-a]pyrazine.

29. The compound according to claim 4 wherein $R_1$ is ortho-chloro and $R_2$ is hydrogen; 8-(2-chlorophenyl)-1,2,4-triazolo[4,3-a]pyrazine.

30. The compound according to claim 4 wherein $R_1$ is para-methoxy and $R_2$ is hydrogen; 8-(4-methoxyphenyl)-1,2,4-triazolo[4,3-a]pyrazine.

31. The compound according to claim 4 wherein $R_1$ is para-methoxy and $R_2$ is methyl; 8-(4-methoxyphenyl)-3-methyl-1,2,4-triazolo[4,3-a]pyrazine.

32. The compound according to claim 4 wherein $R_1$ is para-chloro and $R_2$ is hydrogen; 8-(4-chlorophenyl)-1,2,4-triazolo[4,3-a]pyrazine.

33. The compound according to claim 4 wherein $R_1$ is para-chloro and $R_2$ is methyl; 8-(4-chlorophenyl)-3-methyl-1,2,4-triazolo[4,3-a]pyrazine.

34. The compound according to claim 4 wherein $R_1$ is hydrogen and $R_2$ is hydrogen; 8-phenyl-1,2,4-triazolo[4,3-a]pyrazine.

35. The compound according to claim 4 wherein $R_1$ is hydrogen and $R_2$ is methyl; 8-phenyl-3-methyl-1,2,4-triazolo[4,3-a]pyrazine.

36. A method of treating anxiety in warm-blooded animals comprising administering to said animals an effective amount of a compound of the formula:

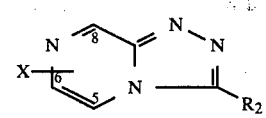

wherein X is

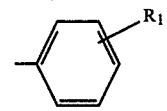

located on the 5, 6 or 8 carbon of said compound and $R_1$ is selected from the group consisting of hydrogen, fluoro, chloro, trifluoromethyl, and $C_1$-$C_3$ alkoxy and wherein $R_2$ is hydrogen or $C_1$-$C_4$ alkyl.

37. The method according to claim 36 wherein said compound is of the formula:

38. The method according to claim 36 wherein said compound is of the formula:

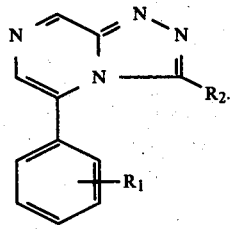

39. The method according to claim 36 wherein said compound is of the formula:

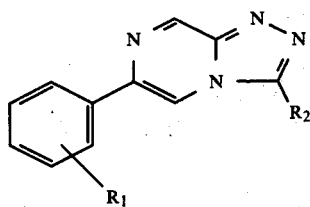

40. The method according to claim 37, claim 38 or claim 39 wherein R₁ is selected from the group consisting of para-ethoxy, ortho-ethoxy, meta-trifluoromethyl, ortho-chloro, ortho-fluoro, para-fluoro, meta-methoxy, para-trifluoromethyl, para-isopropoxy, meta-chloro, para-methoxy and hydrogen.

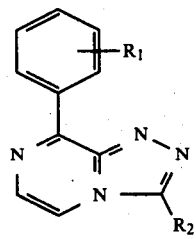

41. The method according to claim 40 wherein R₁ is selected from the group consisting of hydrogen, meta-methoxy and para-chloro.

42. The method according to claim 37, claim 38 or claim 39 wherein R₂ is selected from the group consisting of methyl, ethyl, isopropyl and hydrogen.

43. The method according to claim 36 wherein said compound is administered to said animal in an amount comprising from about 0.5 mg/kg to about 50.0 mg/kg of body weight per day.

44. The method according to claim 36 wherein said compound is administered in dosage units comprising 10 to about 200 mg of said compound.

45. The method according to claim 37 or claim 43 wherein said compound is administered orally to said animal.

46. The method according to claim 45 wherein said compound is administered to said animal in a dosage of about 1.0 mg.kg to about 10 mg/kg of body weight per day.

47. The method according to claim 37 wherein said compound is administered parenterally.

48. The method according to claim 47 wherein said compound is administered in a polyhydric aliphatic alcohol vehicle adapted for parenteral administration containing about 0.01% to about 10.0% by weight of said compound.

49. The method according to claim 37 wherein said compound is administered by intramuscular injection in a vehicle wherein the concentration of said compound is about 25 mg to about 50 mg per ml of the vehicle.

50. The method according to claim 37 wherein said compound is administered intravenously in a vehicle wherein the concentration of said compound is about 5 to about 25 mg per ml of said vehicle.

51. The method according to claim 45 wherein said compound is administered in an assimilable edible carrier wherein said compound comprises about 2 to about 60% by weight of the carrier and compound composition.

52. The method according to claim 37 wherein said compound is 6-phenyl-1,2,4-triazolo[4,3-a]pyrazine.

53. The method according to claim 37 wherein said compound is 6-(3-methoxyphenyl)-1,2,4-triazolo[4,3-a]pyrazine.

54. The method according to claim 37 wherein said compound is 8-(4-chlorophenyl)-1,2,4-triazolo[4,3-a]pyrazine.

* * * * *